(12) United States Patent  (10) Patent No.: US 6,513,529 B1
Kamen  (45) Date of Patent: Feb. 4, 2003

(54) REPULSIVE ANTISEPTIC SURGICAL SHIELD

(75) Inventor: Dean L. Kamen, Bedford, NH (US)

(73) Assignee: Deka Products Limited Partnership, Manchester, NH (US)

( * ) Notice: Subject to any disclaimer, the term of this patent is extended or adjusted under 35 U.S.C. 154(b) by 0 days.

(21) Appl. No.: 09/405,720

(22) Filed: Sep. 24, 1999

Related U.S. Application Data

(60) Provisional application No. 60/102,154, filed on Sep. 28, 1998.

(51) Int. Cl.$^7$ ................................................ A61F 13/00
(52) U.S. Cl. ........................................ 128/847; 128/888
(58) Field of Search ........................... 128/845, 846, 128/847, 849–856

(56) References Cited

U.S. PATENT DOCUMENTS

| | | | | |
|---|---|---|---|---|
| 3,610,238 A | * | 10/1971 | Rich | 128/847 |
| 3,783,588 A | * | 1/1974 | Hudis | 55/126 |
| 3,820,536 A | * | 6/1974 | Anspach | 128/847 |
| 4,275,719 A | * | 6/1981 | Mayer | 128/847 |

* cited by examiner

Primary Examiner—Michael A. Brown
(74) Attorney, Agent, or Firm—Bromberg & Sunstein LLP

(57) ABSTRACT

A method for excluding infectious agents from the site of an incision into the tissue of a patient. Air is the vicinity of the patient is filtered through an ionizing filter, such that any infectious agents in the air are electrically charged with a specified polarity. A region surrounding the site of the incision is thus characterized by an electrostatic charge of the same specified polarity as the infectious agents such that the infectious agents are repelled from the site of the incision. Infectious agents may be excluded from the site of an incision by creating a pressure field of air having a gradient along at least one path running from a zone including the incision to a neighboring zone so that air flows in the direction in the direction of decreasing pressure. A shield system with three layers may be provided, with the first layer substantially electrically insulating and adhering to the skin of the patient while an electrically conductive layer maintains an electrostatic charge of a specified polarity on the shield. An electrically insulating external layer prevents dissipation of the electrostatic charge. The shield system also has an ionizing air filter for charging any infectious agents with an electrical charge of the same specified polarity as the electrostatic charge of the shield for repelling infectious agents from the site of the incision.

5 Claims, 4 Drawing Sheets

REPULSIVE ANTISEPTIC SURGICAL SHIELD

The present application claims priority from U.S. Provisional Application Ser. No. 60/102,154, filed Sep. 28, 1998, and incorporated herein by reference.

TECHNICAL FIELD

The present invention pertains to a device and methods for providing a locally sterile environment at the place of a surgical incision into a living body.

BACKGROUND OF THE INVENTION

Historically, the primary danger attendant to surgical procedures is that of sepsis due to intrusion of microbes into the location where the natural defenses of the body have been breeched by incision. Therefore, extraordinary care is taken to ensure the sterility of the operating environment to the greatest degree achievable. In addition to the sterilization of surgical instruments and the hands and clothing of the surgical team, surgical drapes are employed to provide barriers between the immediate surgical environment and the general operating theater. Additionally, the creation of a barrier zone of filtered air in laminar flow across the surgical area is known in the art, as is the use of a suction tube to remove smoke that may be generated at the site of electrocautery surgery. Finally, U.S. Pat. No. 4,275,719 describes the use of a film sheet in adhesive contact with the skin of the patient at the site of a surgical incision so as to seal a sterilized atmosphere between the film and the body of the patient. The described methods, however, do not actively expel potentially septic materials from the actual site of the incision. It is thus advantageous that a method be provided for actively repelling microbes and other contamination from the immediate vicinity of the incision.

SUMMARY OF THE INVENTION

In accordance with a preferred embodiment of the present invention, there is provided a method for excluding infectious agents from a site of an incision into the tissue of a patient. The method has the steps of filtering air in a vicinity of the patient by passage of the air through an ionizing filter, such that any infectious agents in the air are electrically charged with a specified polarity, and creating a region surrounding the site of the incision characterized by an electrostatic charge of the same specified polarity as the infectious agents such that the infectious agents are repelled from the site of the incision. In accordance with a further embodiment of the invention, a method is provided for excluding infectious agents from the site of an incision by creating a pressure field of air having a gradient along at least one path, each path running from a first zone including the incision to a second zone proximate to the first zone, so that air flows from the incision to the second zone.

In accordance with another aspect of the present invention, there is provided a shield system for excluding infectious agents from a site of an incision through skin of a patient. The shield system has a shield with three layers: a substantially electrically insulating adhesive layer of material for adhesion to the skin of the patient, an electrically conductive layer exterior to the adhesive layer for maintaining an electrostatic charge of a specified polarity on the shield, and an electrically insulating external layer for preventing dissipation of the electrostatic charge. The shield system also has an ionizing air filter for charging any infectious agents with an electrical charge of the same specified polarity as the electrostatic charge of the shield such that any infectious agents are repelled from the site of the incision.

In accordance with a further embodiment of the present invention, there is provided a shield system for excluding infectious agents from a site of an incision through skin of a patient. The shield system, in accordance with this embodiment, has an exterior layer having a thickness and a network of pores, each pore traversing the thickness of the exterior layer, a plenum coupled to each pore of the exterior layer, an adhesive layer of material coupled to the plenum for adhesion to the skin of the patient, and a source of gas coupled to the plenum for pressurizing each pore with respect to an ambient air pressure so as to cause a flow of gas in a direction away from the site of the incision.

In accordance with yet another aspect of the present invention, there is provided a positive-ventilated glove for covering the hand of a surgeon. The glove has an exterior layer having a thickness and a network of pores, each pore traversing the thickness of the exterior layer, a plenum coupled to each pore of the exterior layer, an interior layer of material coupled to the plenum conforming to the hand of the surgeon, and a source of gas coupled to the plenum for pressurizing each pore with respect to an ambient air pressure so as to cause a flow of gas in a direction away from the hand of the surgeon. In an alternate embodiment of the invention, there is provided an electrostatic glove for use by surgical personnel. The glove has a substantially electrically insulating layer of material disposed in contact with the skin of the surgical personnel, an electrically conductive layer exterior to the substantially electrically insulating layer for maintaining an electrostatic charge of a specified polarity on the glove, and an electrically insulating external layer for preventing dissipation of the electrostatic charge such that any infectious agents with an electrical charge of the same specified polarity as the electrostatic charge of the glove are repelled by the glove.

In accordance with yet another aspect of the present invention, there is provided a shield system for excluding infectious agents from a site of an incision through skin of a patient. The shield system has an exterior layer having a thickness and a network of pores, each pore traversing the thickness of the exterior layer, and a plenum coupled to each pore of the exterior layer. The shield system also has a source of gas coupled to the plenum for pressurizing each pore with respect to an ambient air pressure so as to cause a flow of gas in a direction away from the site of the incision, a network of channels disposed substantially in a plane parallel to the skin of the patient for withdrawing air from the site of the incision, and an adhesive layer of material coupled to the plenum and the network of channels for adhesion to the skin of the patient.

BRIEF DESCRIPTION OF THE DRAWINGS

The invention will be more readily understood by reference to the following description, taken with the accompanying drawings, in which.

DETAILED DESCRIPTION OF SPECIFIC EMBODIMENTS

Figure 1:
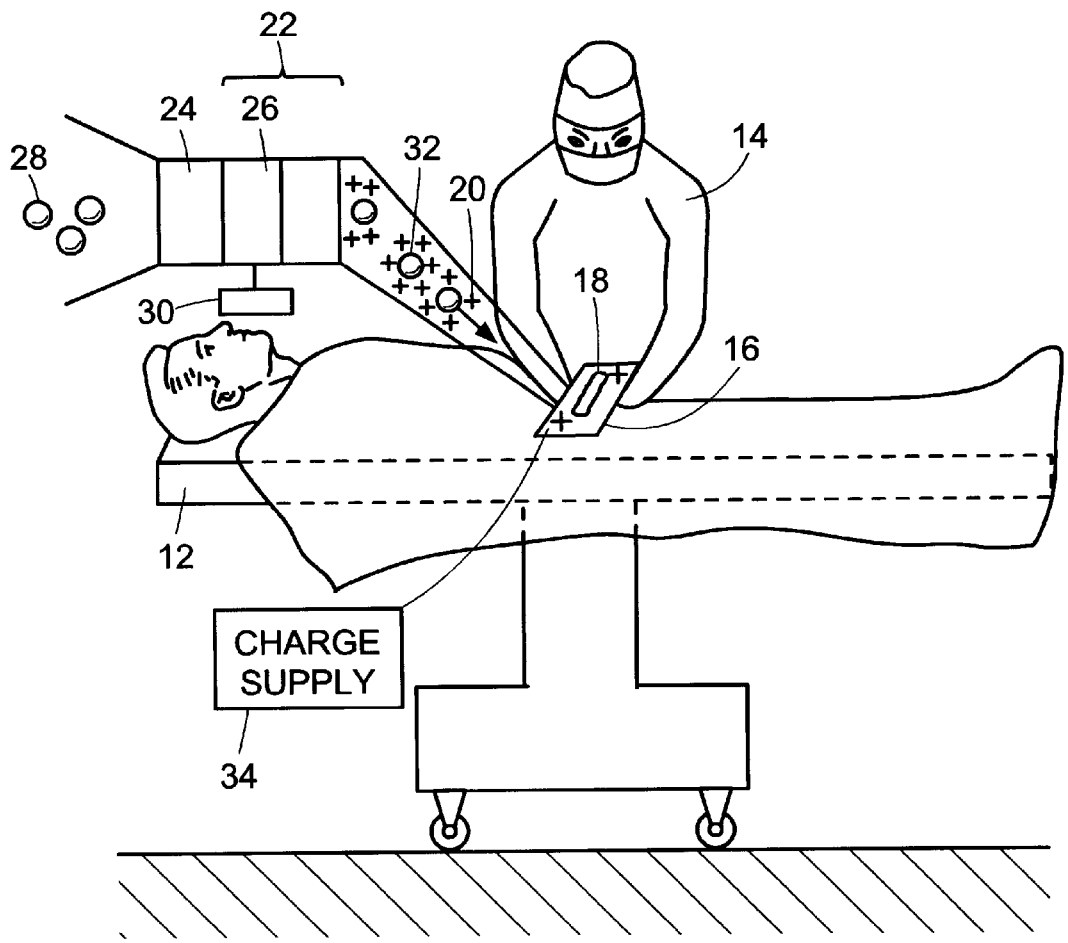
FIG. 1 is a side view of an electrostatic surgical shield system in which ionized particles are repelled from the site of a surgical incision in accordance with a preferred embodiment of the invention.

Preferred embodiments of the present invention may be advantageously employed in sterile environments where surgery is performed on human patients are other living subjects. Additionally, the apparatus and method described may also be advantageously employed where an extremely clean environment must be maintained locally, as in the assembly of critical components for space flight, for example. Referring first to FIG. 1, patient 10 is shown undergoing surgery on operating table 12. Prior to incision through the skin of the patient, surgeon 14 applies a surgical shield 16 to the patient so as to cover the region of the patient's body through which surgery will be performed. Shield 16 is composed of a flexible fabric-like material and has areal dimensions larger than the incision region. Incision into the body is performed by cutting an incision 18 through shield 16, or, alternatively, shield 16 is disposed by surgeon 14 to surround an incision performed into the external tissue of the patient.

Antiseptic action of shield 16 is achieved by providing an electrostatic charge on shield 16 so as to repel electrostatically all particles having the same sign of charge as the electrostatic charge on the shield. Air flow 20 is supplied to the immediate operating environment through ionizing filter 22. Air is impelled through filter 22, for example, by impeller 24, and, more particularly, through one or more ionizers 26. Ionizer 26 may operate on any ionization principle for stripping charge from particles 28 suspended in the air. Such particles include dust and microbial matter. Methods for stripping charge off suspended particles 28 include, for example and without limitation, passing the air through regions of intense electrical field, created either in DC or AC electrical discharges, with voltage supplied by power supply 30, or in microwave-induced discharges. Stripping electrical charge off particles 28 leaves a positive electrical charge on such particles 32 as are blown in air supply 20 into the operating environment. Particles 32 are repelled from the proximity of shield 16 by virtue of shield 16 having a net electrical charge, supplied by charge supply 34, of the same polarity as the charge imparted to particles 32 by ionizing filter 22.

Figure 2:
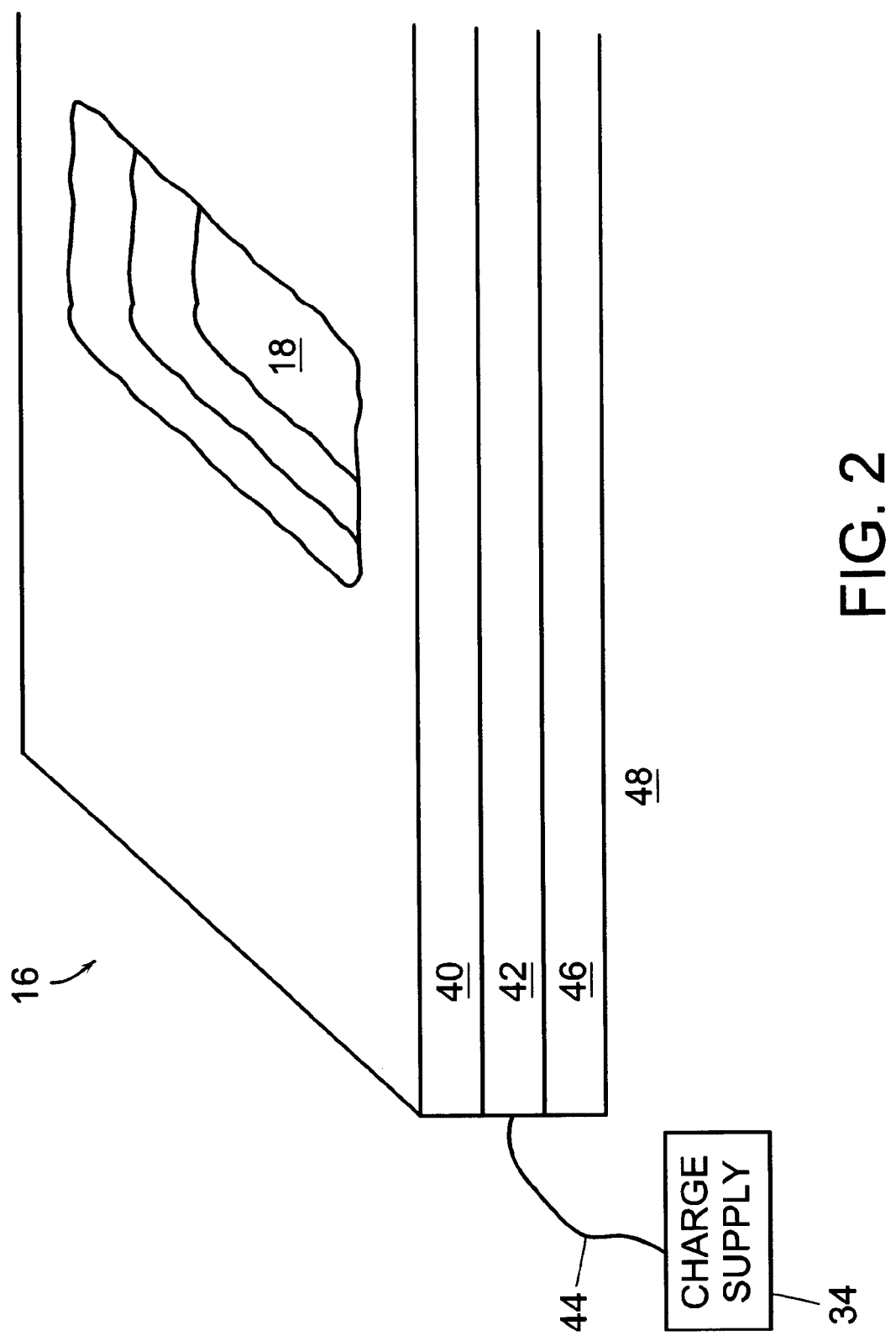
FIG. 2 is a perspective view of an electrostatically repulsive shield showing an incision having been cut for access to internal tissue of surgical patient.

Referring now to FIG. 2, a section of shield 16 is shown, with incision 18 cut away to allow surgical operation on a patient through the shield. Shield 16 is comprised of three layers, now described, of flexible fabric-like material. An outer layer 40 is exposed to the air and is electrically insulating to prevent dissipation of the electrical charge on the shield through contact with surgical personnel or implements. Outer layer may be a polymer fabric or a polymer/textile composite, for example. An intermediate layer 42 of the shield bears electrostatic charge and is composed of a material, such as a metal weave, for example, which is substantially electrically conducting so that the charge imparted by charge supply 34 via conducting wire 44 may be apportioned over the entire area of the layer. An adhesive layer 46 is disposed between intermediate layer 42 and skin surface 48 of the patient. Adhesive layer 46 is an electrically insulating fabric-like material, such as a polymer or textile, so that the electrical charge is not dissipated through skin surface 48. Additionally, layer 46 is adhered to skin 48 by any adhesive means commonly used for adhering bandages to the skin.

To calculate a typical amount of charge required to eliminate particles from the vicinity of a wound, one may assume a particle within an order of magnitude of 1 $\mu$m in linear dimension and specific density on the order of unity, leading to a mass per particle on the order of $10^{-12}$ gm. Electrostatic energies, of order qV, where q is the charge imposed on the particle and V is the electrostatic potential on the shield, dominate gravitational energies and thermal energies (~kT, where k is the Boltzmann constant and T is the temperature) associated with Brownian motion in the air. Thus, it is only necessary to ensure that the electrostatic repulsive force due to the charge on the shield is such that a particle never approaches the shield surface and not become neutralized by conduction.

Figure 3:
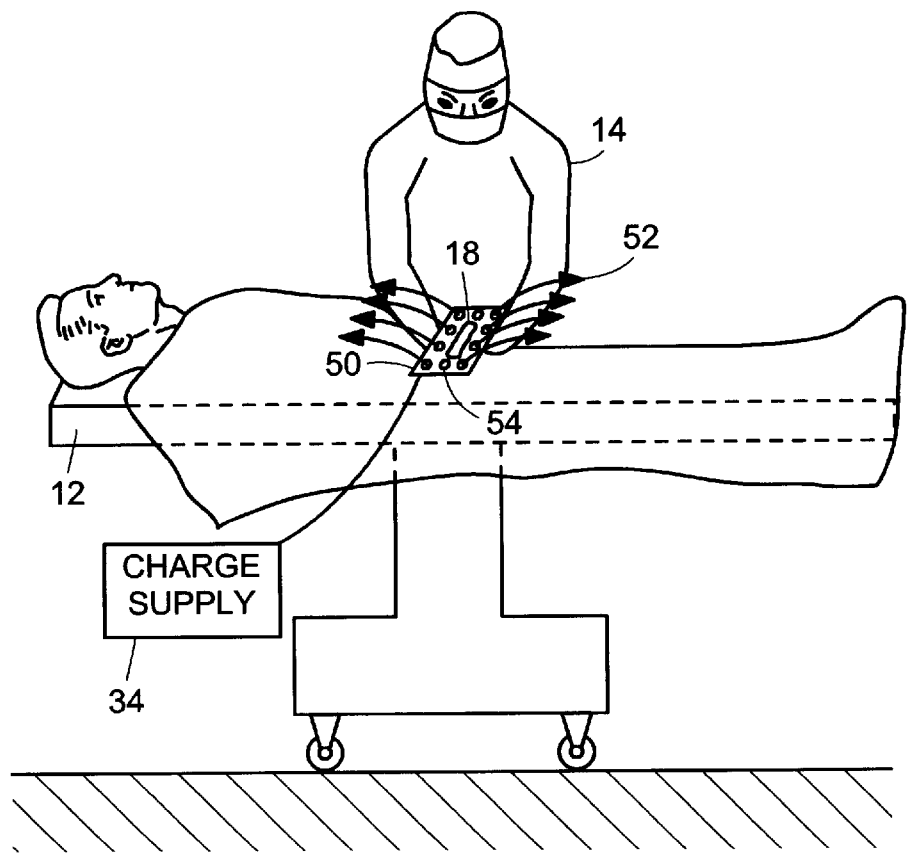
FIG. 3 is a side view of a pressurized surgical shield system in which air is driven from the site of a surgical incision in accordance with a preferred embodiment of the invention.

Referring to FIG. 3, in accordance with an alternate embodiment of the invention, patient 10 is again shown undergoing surgery on operating table 12. Prior to incision through the skin of the patient, surgeon 14 applies a surgical shield 50 to the patient so as to cover the region of the patient's body through which surgery will be performed. Shield 50 is again composed of a flexible fabric-like material and has areal dimensions larger than the incision region. Incision into the body is performed by cutting an incision 18 through shield 50, or, alternatively, shield 50 is disposed by surgeon 14 to surround an incision performed into the external tissue of the patient.

Antiseptic action of shield 50 is achieved by providing a plurality of currents of air so as convey particles away from the vicinity of the incision. Air flow 52 away from incision 18 may be provided through pores 54 in shield 50.

Figure 4:
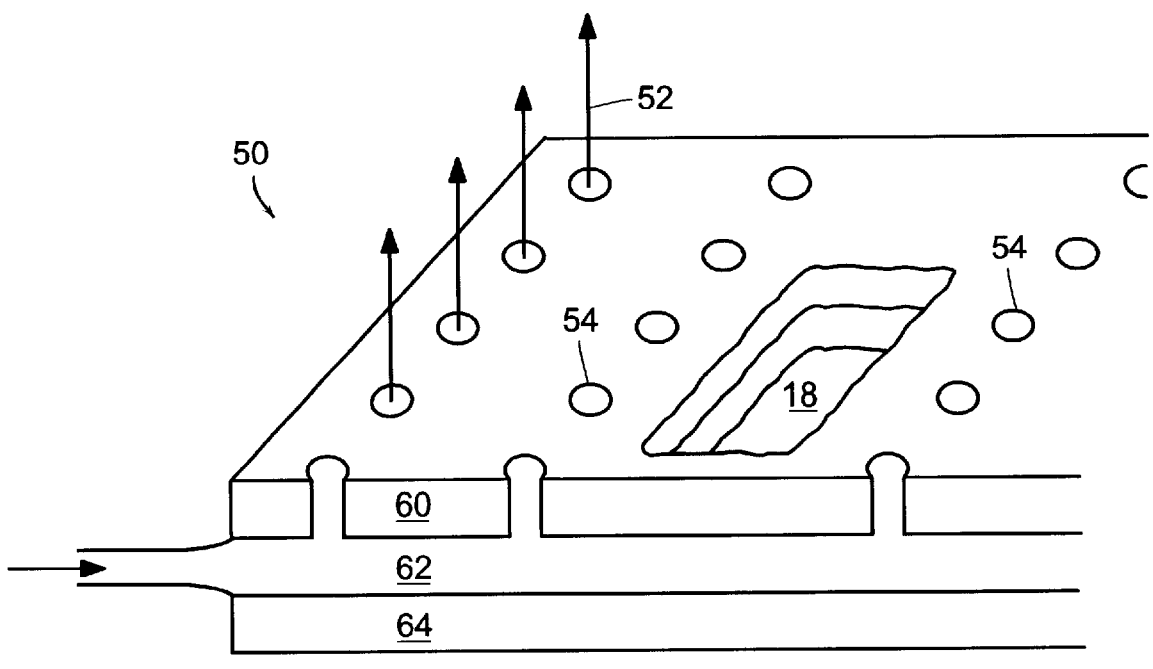
FIG. 4 is a perspective view of a pressurized repulsive shield showing an incision having been cut for access to internal tissue of the surgical patient.

Referring now to FIG. 4, a section of shield 50 is shown, with incision 18 cut away to allow surgical operation on a patient through the shield. Shield 50 is comprised of three layers, now described, of flexible fabric-like material. An outer layer 60 is exposed to the air and is punctuated by pores 54 spaced on a regular grid or otherwise which traverse the thickness of outer layer 60. Outer layer may be a polymer fabric or a polymer/textile composite, for example. An intermediate layer 62 of the shield is a plenum through which air or other pressurized gas, preferably filtered to ensure sterility, may be supplied to create an overpressure at pores 54, thereby causing a net air flow 52 away from shield 50 and thus away from the region of incursion into the external body tissue of the patient. An adhesive layer 64 is disposed between intermediate layer 62 and skin surface 48 of the patient. Adhesive layer 64 may be substantially impervious to flowthrough of pressurized gas toward skin 48 but need not be absolutely impenetrable. Adhesive layer 64 may be a polymer or textile, for example. Layer 64 is adhered to skin 48 by any adhesive means commonly used for adhering bandages to the skin.

Figure 5:
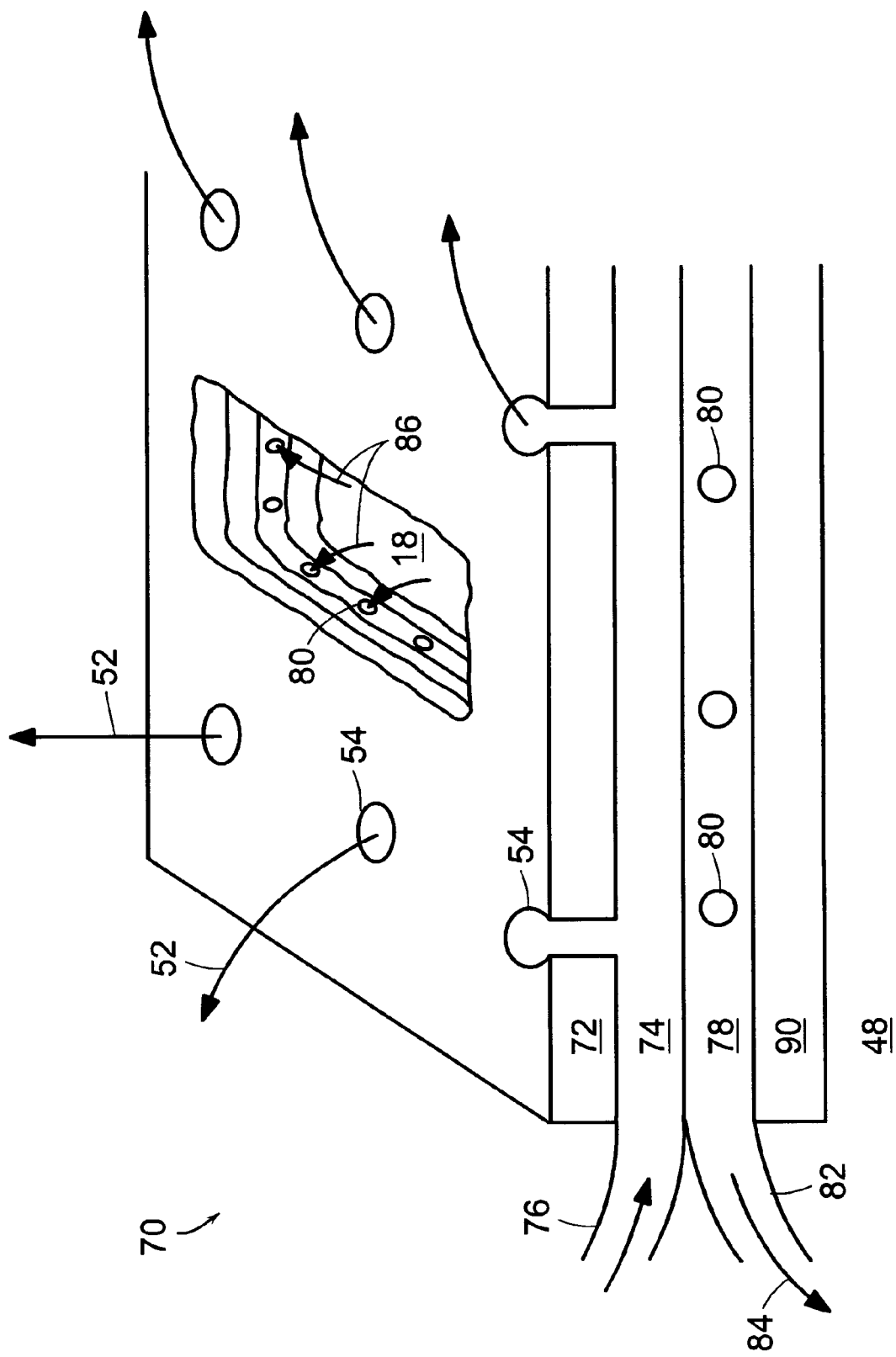
FIG. 5 is a perspective view of a pressurized repulsive shield having suction channels severed by an incision for access to internal tissue of the surgical patient.

Referring now to FIG. 5, in accordance with yet another alternate embodiment of the invention, a combination of overpressure and suction with respect to the ambient air pressure may be advantageously employed for protection of a body incision from sepsis. A section of shield 70 is shown, with incision 18 cut away to allow surgical operation on a patient through the shield. Shield 70 is comprised of four layers, now described, of flexible fabric-like material, of which the central two are plena, respectively, for overpressure and suction with respect to the ambient air pressure. An outer layer 72 is exposed to the air and is punctuated by pores 54 spaced on a regular grid or otherwise which traverse the thickness of outer layer 72. Outer layer may be a polymer fabric or a polymer/textile composite, for example. A first intermediate layer 74 of the shield is a plenum through which air or other pressurized gas, preferably filtered to ensure sterility, may be supplied via hose 76 to create an overpressure at pores 54, thereby causing a net air flow 52 away from shield 70 and thus away from the region of incursion into the external body tissue of the patient. A second intermediate layer 78 is a plenum containing a network of channels 80 running within the plane of the layer, substantially parallel to skin surface 48 of the patient. Suction is applied to channels 80 via hose 82 creating a net flow 84 away from incision 18. Incision 18 severs channels 80 so that the underpressure within the channels causes a local flow of air 86 away from the wound. Adhesive layer 90 is disposed between intermediate layers 74 and 78 and skin surface 48 of the patient. Adhesive layer 90 may be substantially impervious to flowthrough of pressurized gas toward skin 48 but need not be absolutely impenetrable, and is adhered to skin 48 by any adhesive means commonly used for adhering bandages to the skin.

Clearly, an advantageous mode of employing the present teachings is an embodiment in which the foregoing electrostatic and fluid mechanical repulsions are employed in combination.

In accordance with another alternate embodiment of the invention, surgical shields described above in reference to FIGS. 2 or 4 may be incorporated into gloves worn by the surgeon, thereby repelling potentially infectious matter from the vicinity of the incision.

The described embodiments of the invention are intended to be merely exemplary and numerous variations and modifications will be apparent to those skilled in the art. All such variations and modifications are intended to be within the scope of the present invention as defined in the appended claims.

I claim:

1. A method for excluding infectious agents from a site of an incision into the tissue of a patient, the method comprising:
   a. filtering air in a vicinity of the patient by passage of the air through an ionizing filter, such that any infectious agents in the air are electrically charged with a specified polarity;
   b. creating a region surrounding the site of the incision characterized by an electrostatic charge of the same specified polarity as the infectious agents such that the infectious agents are repelled from the site of the incision.

2. A method for excluding infectious agents from the site of an incision, the method comprising:
   a. creating a pressure field of air having a gradient along at least one path, each path running away from a first zone including an area surrounding the incision to a second zone proximate to the first zone, so that air flows from the vicinity of the incision to the second zone.

3. A shield system for excluding infectious agents from a site of an incision through skin of a patient, the shield system comprising:
   a. a shield comprising:
      i. a substantially electrically insulating adhesive layer of material for adhesion to the skin of the patient;
      ii. an electrically conductive layer exterior to the adhesive layer for maintaining an electrostatic charge of a specified polarity on the shield; and
      iii. an electrically insulating external layer for preventing dissipation of the electrostatic charge; and
   b. an ionizing air filter for charging any infectious agents with an electrical charge of the same specified polarity as the electrostatic charge of the shield such that any infectious agents are repelled from the site of the incision.

4. A shield system for excluding infectious agents from a site of an incision through skin of a patient, the shield system comprising:
   a. an exterior layer having a thickness and a network of pores, each pore traversing the thickness of the exterior layer;
   b. a plenum coupled to each pore of the exterior layer;
   c. an adhesive layer of material coupled to the plenum for adhesion to the skin of the patient; and
   d. a source of gas coupled to the plenum for pressurizing each pore with respect to an ambient air pressure so as to cause a flow of gas in a direction away from the site of the incision.

5. A shield system for excluding infectious agents from a site of an incision through skin of a patient, the shield system comprising:
   a. an exterior layer having a thickness and a network of pores, each pore traversing the thickness of the exterior layer;
   b. a plenum coupled to each pore of the exterior layer;
   c. a source of gas coupled to the plenum for pressurizing each pore with respect to an ambient air pressure so as to cause a flow of gas in a direction away from the site of the incision;
   d. a network of channels disposed substantially in a plane parallel to the skin of the patient for withdrawing air from the site of the incision; and
   e. an adhesive layer of material coupled to the plenum and the network of channels for adhesion to the skin of the patient.

* * * * *